Figure 1:
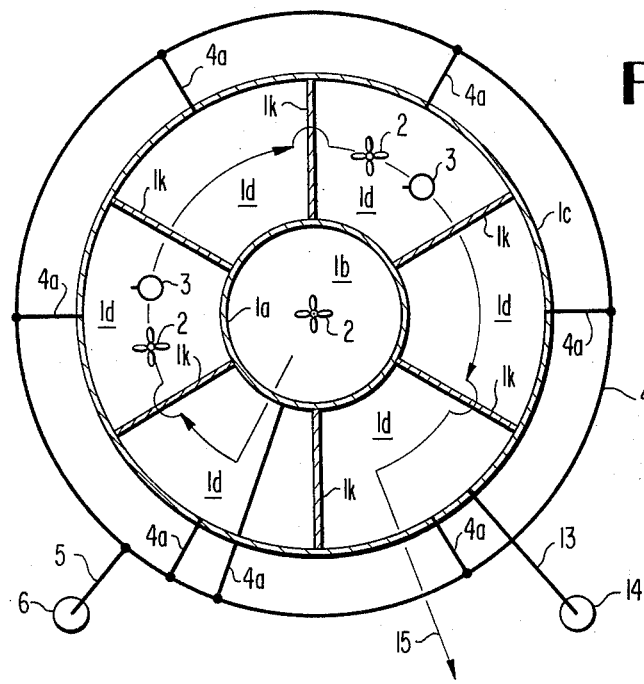

United States Patent [19]

Saffran et al.

[11] 4,055,577

[45] Oct. 25, 1977

[54] PROCESS FOR THERMAL TREATMENT OF CRUDE PHTHALIC ACID

[75] Inventors: Helmut Saffran, Dansweiler; Lothar Sterck, Hurth, both of Germany

[73] Assignee: Davy Powergas GmbH, Cologne, Germany

[21] Appl. No.: 522,913

[22] Filed: Nov. 11, 1974
(Under 37 CFR 1.47)

[51] Int. Cl.$^2$ ............................................. C07D 307/89
[52] U.S. Cl. .................................. 260/346.7; 202/173
[58] Field of Search ....................... 260/346.7; 202/173

[56] References Cited

U.S. PATENT DOCUMENTS

| | | | |
|---|---|---|---|
| 2,658,029 | 11/1953 | Untermann et al. | 202/173 |
| 2,704,742 | 3/1955 | Petrich | 202/173 |
| 3,428,423 | 2/1969 | Egbert | 260/346.7 |
| 3,507,886 | 4/1970 | Suter et al. | 260/346.7 |
| 3,655,521 | 4/1972 | Gehrken et al. | 260/346.7 |

*Primary Examiner*—John D. Randolph
*Attorney, Agent, or Firm*—Bernard & Brown

[57] ABSTRACT

There is disclosed a process and apparatus for the thermal treatment of crude phthalic anhydride. The process is conducted in a system with an inner chamber and outer chamber positioned therearound and the chambers have a common wall. The outer chamber may be divided into a plurality of sub-chambers and the flow of the phthalic anhydride undergoing treatment may be substantially reversed in successive ones of the sub-chambers. The system provides for more efficient use of heat and equipment.

17 Claims, 2 Drawing Figures

PROCESS FOR THERMAL TREATMENT OF CRUDE PHTHALIC ACID

This invention relates to a process and an apparatus for the thermal treatment of crude phthalic anhydride to enhance its purification. In the invention, the crude phthalic anhydride is treated in a system having an outer thermal zone which is positioned around an inner zone. The crude phthalic anhydride passes through these zones and the system more efficiently utilizes the heat and equipment.

Crude phthalic anhydride obtained in the catalytic, air oxidation of hydrocarbons such as o-xylene or naphthalene, contains small amounts of by-products including carboxylic acids such as maleic acid, phthalic acid, fumaric acid, benzoic acid, and o-toluic acid, phthalide and aldehydes, as well as unreacted hydrocarbon feed. If naphthalene is used as the feed material, there is a particular presence of naphthoquinone. Prior to the purification of the crude product through distillation, it is subjected expediently to a thermal treatment at elevated temperatures, e.g., between about 190° and 285° C. During such treatment for purification purposes, by-products are converted to materials which are more readily separated from the phthalic anhydride, and phthalic acid and maleic acid are dehydrated to their anhydrides. Also, fumaric acid is decarboxylated and naphthoquinone is resinified to non-volatile products. At least part of the more volatile compounds contained in the crude phthalic anhydride, such as maleic acid anhydride, benzoic acid and unreacted hydrocarbons can be separated as vapors withdrawn from the material undergoing treatment.

In the past, such crude phthalic anhydride products have been heated in a stirred vessel or in a plurality of vessels arranged in cascade fashion in order to split-off and remove water along with impurities that boil at lower temperatures than phthalic anhydride. With a single stirred vessel, one can work successfully only in a discontinuous manner since continuous operation does not produce sufficient purification of the crude feed. Moreover, when a plurality of vessels is used in a manner providing for cascade flow from one vessel to another of the material undergoing treatment, the cost of the apparatus is considerable. Since the temperature of the treatment is substantially above room temperature, considerable heat losses are also experienced when one uses a cascading, stirred vessel arrangement.

The present invention is directed to a process and an apparatus for the thermal treatment of crude phthalic anhydride materials of the types described above, and the invention facilitates good purification of the crude substance with less cost than experienced when using the normal stirred vessel, cascade system. The present invention also provides a more economic operation due to less loss of heat from the operation. These advantages are obtained by conducting the thermal treatment as the crude phthalic anhydride passes through an outer chamber which is positioned around an inner chamber having a common wall with the outer chamber to facilitate heat exchange between the liquid materials in these chambers. The thermal treatment is conducted at an elevated temperature, e.g. about 190° to 285° C., and for a period of time, sufficient to enhance the purification of the crude phthalic anhydride without undue degradation of phthalic anhydride product. Such treatment converts oxidation by-product impurities in the crude feed and removes unreacted hydrocarbons and water according to one or more of the mechanisms described above in connection with past thermal treatment of the crude feedstock. The product, which is thermally treated according to this invention, can be purified by further treatment such as by distillation. In comparison with thermal treatment in a cascade arrangement of separate containers, the flow of the crude phthalic anhydride through the equipment of the present invention gives the desired thermal treatment with the exposure of a lesser amount of external surface of the treating zone to the ambient atmosphere and, as a result, there is less loss of heat to the surroundings.

According to one preferred embodiment of the invention, the crude phthalic anhydride is passed from the outer chamber into the inner chamber from which it is removed for further purification or use. This procedure is particularly expedient, if the highest temperature in the outer chamber is maintained toward the end of the flow path of the phthalic anhydride through this chamber, and thus, the warmer inner or central chamber is surrounded by the less warm outer chamber. According to another embodiment of the invention, the crude phthalic anhydride feed is charged into the central chamber and, from there, it is introduced into the outer chamber. The thermally treated product is removed, in this case, from the outer chamber.

In one apparatus of the invention, the inner zone forms a central chamber and is substantially completely surrounded by a larger, outer, thermal treating zone which may be an annular chamber having a common wall with the inner chamber. A substantially radial partition is positioned between this common wall and the outer wall of the outer chamber. The flow of the crude phthalic anhydride through the outer chamber is then from adjacent one side of this partition through substantially the entire outer chamber to the other side of this partition. Preferably, the outer chamber is divided into a plurality of subchambers by one or more additional, substantially radial, partitions positioned between the said common wall of the inner and outer chambers and the outer wall of the latter. These subchambers are arranged to provide for serial flow of the phthalic anhydride from one sub-chamber to another. This flow can be through an opening in the partitions or by the liquid phthalic anhydride stream passing above or beneath a given partition. The vapor spaces above the inner chamber and above the outer chamber, or the subchambers thereof, can be in communication so that vapor can be withdrawn from all of these spaces by a common piece of equipment, e.g. a vacuum pump. The crude phthalic anhydride can travel between the inner and outer chambers through an opening in the common wall therebetween. The treated product can be withdrawn from the inner chamber and passed, for instance, to distillation apparatus. The reverse direction of flow of the phthalic anhydride stream through the inner and outer chambers is, likewise, permissible to accomplish the desired thermal treatment.

If the outer chamber is divided by two or more partitions into a plurality of sub-chambers, say in the form of annular sections, the crude phthalic anhydride product can flow in sequence through every sector-chamber of this kind, and then pass into the central chamber. The reverse flow is also possible in this case. The dividing partitions can contain openings for the passage of the phthalic anhydride; however, the partition dividing the outer chamber immediately adjacent the fluid inlet and outlet for this chamber generally does not contain an opening, or otherwise permit the passage of significant amounts of liquid past this partition. Thus, the flow passes from one side of such a partition through substantially the entire outer chamber to the other side of this partition. Compared to the known use of a cascade of separate containers for conducting the thermal treatment, the apparatus of the invention is characterized by a considerable saving of material of construction and cost of manufacture. The compact arrangement of the inner and outer chambers reduces not only the floor and space requirements of the apparatus, but also effects a reduced loss of heat to the surroundings, so that the total heat requirement for the treatment is reduced.

According to a preferred embodiment of the invention, the inner and outer chambers are cylindrical and circular in cross-sectional shape, and the two chambers advantageously have approximately the same height. The inner and outer chambers are thus arranged concentrically to one another, so that the annular or outer chamber has the same cross-sectional dimension throughout its entire length, and the velocity of the flow of the phthalic anhydride stream along the length of its path is substantially constant or equal. It is another preference in the invention that the partitions in the outer chamber past which the phthalic anhydride flows, have openings for the flow which provide for reversing the directions of flow past successive partitions so that the flow in adjacent subchambers is in substantially opposite directions, e.g. upwardly in one sub-chamber and downwardly in the adjacent sub-chamber. By this arrangement, the paths for all portions of fluid traveling through the outer chamber are more equal, and the times that all given portions of the phthalic anhydride are subjected to the thermal treatment are more uniform.

As previously stated, the upper portions of the inner and outer chambers, i.e., the gas or vapor spaces thereof, are expediently connected to one another and, by means of a suction line, to a vacuum pump. This interconnection of the separate chambers can be arranged by providing openings in the walls or partitions in the area of the gas space. It is also possible to have alternate partitions in the outer chamber end slightly below the level of liquid phthalic anhydride to permit overflow from one sub-chamber to another, while the other alternate partitions allow underflow between successive sub-chambers. The latter partitions may end at a position somewhat above the bottom of the outer chamber and slightly above the level of liquid, but below the top of the outer chamber, so that a sufficient gap for the free passage of gas remains between the upper edge of partitions and the cover of the treatment installation. A single suction pipe is then sufficient for drawing off the volatile materials that are formed during the flow of the crude product through the apparatus of the invention, e.g., water, carbon dioxide, maleic anhydride, benzoic acid and unreacted hydrocarbons. The pressure in the gas space above the liquid crude product is advantageously about 400 to 760 torr, preferably about 550 to 750 torr. The gases drawn off may pass through a condenser that is kept at a temperature, e.g., between about 140° and 170° C., which causes condensation of phthalic anhydride that may be volatilized. The condensate obtained can be led back into the thermal treatment system, preferably into the chamber which is first in regard to liquid flow of the crude feed.

According to a preferred embodiment of the invention, a plurality, say up to about six, preferably two to four or six, substantially radial partitions are arranged in the outer chamber to divide it into an equal number of sub-chambers. The partitions extend between the common wall of the inner and outer chambers and the outer wall of the outer chamber. The subdivision of the outer chamber into separate sub-chambers produces a greater uniformity in the residence time of each portion of the crude product in the thermal treatment system. As a result, the purified product contains a more constant, low amount of impurities, that can be readily separated through subsequent distillation. The outer chamber is expediently subdivided in such a manner that the amount of liquid in each individual sub-chamber thus formed is approximately the same volume as in the inner chamber. According to a preferred embodiment of the invention, the inner chamber is the last chamber in regard to flow of the phthalic anhydride undergoing thermal treatment, and the inner chamber is provided with an outlet connection for withdrawing the thermally-treated, liquid phthalic anhydride. Since the highest thermal treatment temperature generally prevails in the last chamber, the heat losses to the surroundings are the lowest when the highest temperature prevails in the inner chamber. The side walls of the inner container do not require thermal insulation, since the heat which passes through is absorbed by the crude phthalic anhydride that is flowing through the outer chamber.

According to a preferred embodiment of the invention, it is provided further that at least one of the inner and outer chambers in the thermal treating system be equipped with a discharge line which is connected through a return line and heater to the first chamber used for thermally treating the crude phthalic anhydride. The thus recycled phthalic anhydride from the thermal treatment chambers can thus be circulated through the heater, and the desired temperature can thereby be provided in the chamber which is first in regard to crude phthalic anhydride flow. In an advantageous arrangement, each sub-chamber of the outer chamber, and preferably the inner chamber, is equipped with a discharge line which is connected to the heater for heating and recycling of withdrawn liquid phthalic anhydride to the thermal treatment system. The amount of material circulated from the separate chambers can be adjusted separately by means of valves in each of the discharge lines from such chambers.

The invention is described more in detail below by reference to the drawings.

Figure 2:
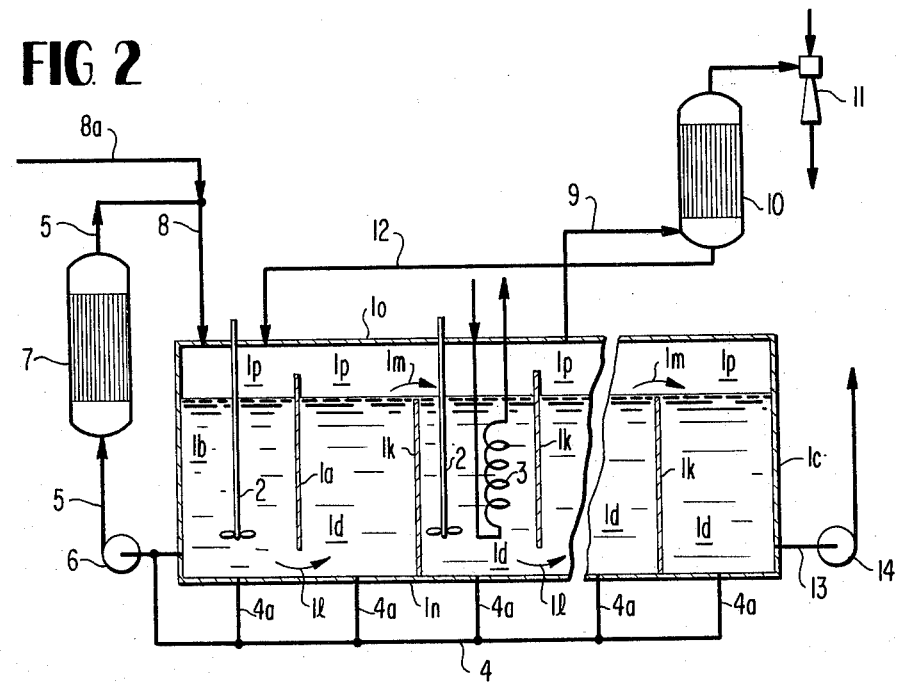

FIG. 1 shows a schematic representation of an apparatus of the invention in plan view, and FIG. 2 shows a schematic representation of the apparatus of the invention in side elevation, in which, for illustrative purposes, the chambers traversed successively by the phthalic anhydride flow are shown in sequence from left to right, rather than in their actual inner and outer arrangement as shown, for example, in FIG. 1.

In the embodiment of the apparatus of the invention, illustrated in the drawings, a circular, cylindrical inner chamber 1b, formed by metal wall 1a, is surrounded concentrically by a circular, cylindrical outer chamber formed by the wall 1c. The annular space between the two containers is subdivided through six radial partitions 1k into six annular-sector sub-chambers 1d, each having the same volume of liquid therein, which volume is the same as in chamber 1b. It is generally preferred that the volume of liquid in the inner chamber be at least about one-tenth of the volume of liquid in the total outer chamber. The maximum volume of liquid in the inner chamber usually does not exceed the volume of liquid in the total outer chamber. The central chamber 1b, as well as a plurality of annular-sector sub-chambers 1d, are provided with heaters 3 as shown in FIG. 1.

The wall between inner chamber 1b, adjacent to the sub-chamber 1d receiving flow from inner chamber 1b as shown in FIG. 1, as well as partitions 1k between annular-sector sub-chambers 1d, are provided with alternate underflows and overflows 1s and 1m, respectively. However, the partition 1k between the first and last subchambers 1d in the path of flow of the liquid phthalic anhydride, as shown in FIG. 1, completely blocks the flow of liquid, but not vapor flow, between these sub-chambers. Partitions 1k and the walls of inner chamber 1b do not extend to the cover 1o of the entire tank installation, so the gas spaces above chambers 1b and 1d are interconnected. Gas spaces 1p are connected to a vacuum pump 11 through a line 9. This line contains condenser 10, wherein the phthalic anhydride present in the gases drawn-off is condensed. The condensate is led back into central chamber 1b through line 12. The readily-volatile components that are drawn off, such as water, carbon dioxide, maleic acid anhydride, benzoic acid, and hydrocarbons pass through condenser 10 and may possibly be separated, even before reaching vacuum pump 11, in a sublimation device that is not shown.

The crude phthalic anhydride is continuously fed to central chamber 1b through lines 8a and 8. A return or recycle line 5, having pump 6 and heater 7, enables the temperature to be controlled in central chamber 1b by heating recycled phthalic anhydride. Pipe 4 has connections 4a arranged below the bottom 1n of both the inner chamber and outer sub-chambers so that phthalic anhydride can be removed from each of the separate chambers and circulated through line 5, pump 6, heater 7, and line 8, for return to the inner chamber 10 in an amount sufficient to maintain the desired temperature in the inner and outer chambers. The thermally-treated product is continuously removed from sub-chamber 1d, which is last in the line of flow, through a line 13 by a pump 14 and line 15, and supplied to a distillation installation (not shown) for further purification of the phthalic anhydride.

In the embodiment illustrated in the drawings, the liquid phthalic anhydride undergoing thermal treatment flows from central chamber 1b along the indicated flow path in the direction of the arrows to line 15 through annular-sector sub-chambers 1d. The reverse direction of flow is also permissible and may be advantageous, especially if the highest temperature of thermal treatment prevails in the inner chamber, which would be the last in regard to liquid flow.

The process and apparatus of the invention are characterized by a number of advantages compared to the thermal treatment of crude phthalic anhydride in a stirred-vessel, cascade arrangement, namely, through the lower cost of equipment, less floor space requirement for supporting the installation, and, in particular, less requirement of heat for maintaining the temperature of treatment which is the result of reduced losses of heat to the surrounding atmosphere.

The invention and its advantages are described further with reference to the following examples.

EXAMPLE

An apparatus of the invention, having a total volume of 100 cubic meters and having its annular outer chamber subdivided into four quadrants that are equal in size to each other and to the central or inner chamber, is traversed by the flow of crude phthalic anhydride amounting to 11.8 tons per hour. The external diameter of the apparatus is 4.9 meters, its height is 5.4 meters, and the outer diameter of its central chamber 2.2 meters. This apparatus requires 177 square meters of wall material of construction, and 81 square meters of insulating material to cover only the outer wall. The floor space requirement of this installation amounts to about 19 square meters. In order to heat the phthalic anhydride, which is passed through this apparatus, from 160° to 270° C., one needs $5.40 \times 10^5$ kcal./hour, inclusive of the heat losses, the latter amounting to $0.2 \times 10^5$ kcal./hour.

COMPARATIVE EXAMPLE

If one subjects to thermal treatment 11.8 tons per hour of crude phthalic anhydride in a cascade consisting of five serially-connected containers, each having a volume of 20 cubic meters, a diameter of 2.85 meters and a height of 3.15 meters. The entire cascade requires 207 square meters of wall material of construction and 141 square meters of insulating material. The total floor space requirement for these containers amounts to 32 square meters. At the throughput of crude phthalic anhydride indicated, the entire installation requires $5.55 \times 10^5$ kcal./hour of heat to raise the temperature of the material from 160° to 270° C., of which $0.35 \times 10^5$ kcal./hour is for the compensation of the heat losses.

This comparison shows that the following savings can be realized by the use of the invention: about 15% in regard to wall material of construction, about 40% for insulating material, about 40% in regard to floor space requirement, and about 40% for the heat expenditure required to compensate for heat losses. To this, one can add the savings in the transportation, assembly and piping for the apparatus of this invention.

It is claimed:

1. A process for the thermal treatment of crude liquid phthalic anhydride to enhance purification of said liquid which comprises passing said liquid through a portion of a thermal treating path, passing said liquid from said portion through another portion of said path, one of said portions being positioned substantially completely around said other portion and in adjacent, indirect heat exchange relationship therewith, and heating said liquid as it passes through said path to a temperature of about 190° to 285° C.

2. The process of claim 1 in which said portion positioned substantially completely around said other portion is annular.

3. The process of claim 1 in which said liquid is passed from one said portion through said other portion positioned substantially completely therearound.

4. The process of claim 1 in which said liquid is passed through one said portion positioned substantially completely around said other portion, and into said latter portion.

5. The process of claim 4 in which said other portion is at a higher temperature than said portion positioned substantially completely therearound.

6. The process of claim 5 in which said other portion has a lesser volume than said portion positioned substantially completely therearound.

7. The process of claim 1 wherein said portion positioned substantially completely around said other portion comprises a plurality of sub-portions, and the flow of liquid phthalic anhydride through said sub-portions in serial and in substantially opposite vertical directions in adjacent ones of said plurality of sub-portions.

8. The process of claim 7 in which said portion positioned substantially completely around said other position is annular.

9. The process of claim 7 in which said liquid is passed from one said portion through said other portion positioned substantially completely therearound.

10. The process of claim 7 in which said liquid is passed through one said portion positioned substantially completely around said other portion, and into said latter portion.

11. The process of claim 10 in which said portion positioned substantially completely around said other portion is comprised of two to six sub-portions.

12. The process of claim 11 in which said liquid phthalic anhydride is withdrawn from one or more of said sub-portions, and withdrawn liquid phthalic anhydride is recycled to said portion to which said liquid phthalic anhydride is initially fed.

13. The process of claim 1 in which vapors from said liquid phthalic anhydride are withdrawn from said portions of said path.

14. A process for the thermal treatment of crude liquid phthalic anhydride to enhance purification of said liquid which comprises passing said liquid through a first portion of a thermal treating path, passing said liquid from said first portion through another portion of said path in which the liquid therein is at a higher temperature than in said first portion, one of said portions being a central portion and another of said portions being positioned substantially completely around said central portion and in adjacent, indirect heat exchange relationship therewith, heating said liquid passing through said path, said liquid passing through said portion positioned substantially completely around said central portion being in indirect heat exchange flow with respect to said central portion to transfer heat from said liquid which is at a higher temperature to liquid in said path at a lower temperature, and withdrawing thermally treated liquid from said path.

15. The process of claim 14 in which said central portion is at a higher temperature than said portion therearound.

16. The process of claim 14 in which said central portion is at a lower temperature than said portion therearound.

17. The process of claim 14 in which said liquid is heated to about 190° to 285° C.

* * * * *